United States Patent
Chen et al.

(10) Patent No.: US 10,925,495 B2
(45) Date of Patent: Feb. 23, 2021

(54) APPARATUS AND METHOD FOR DETERMINING A BLOOD PRESSURE OF A SUBJECT

(71) Applicant: BOE TECHNOLOGY GROUP CO., LTD., Beijing (CN)

(72) Inventors: Xue Chen, Beijing (CN); Guohe Wang, Beijing (CN)

(73) Assignee: BOE TECHNOLOGY GROUP CO., LTD., Beijing (CN)

( * ) Notice: Subject to any disclaimer, the term of this patent is extended or adjusted under 35 U.S.C. 154(b) by 400 days.

(21) Appl. No.: 15/766,987

(22) PCT Filed: May 4, 2017

(86) PCT No.: PCT/CN2017/083055
§ 371 (c)(1),
(2) Date: Apr. 9, 2018

(87) PCT Pub. No.: WO2018/201395
PCT Pub. Date: Nov. 8, 2018

(65) Prior Publication Data
US 2019/0059753 A1    Feb. 28, 2019

(51) Int. Cl.
| | | |
|---|---|---|
| *A61B 5/021* | (2006.01) | |
| *A61B 5/00* | (2006.01) | |
| *A61B 5/024* | (2006.01) | |
| *A61B 5/0245* | (2006.01) | |
| *A61B 5/0456* | (2006.01) | |

(52) U.S. Cl.
CPC ........ *A61B 5/02125* (2013.01); *A61B 5/0245* (2013.01); *A61B 5/02416* (2013.01);
(Continued)

(58) Field of Classification Search
CPC ............ A61B 5/02116; A61B 5/02125; A61B 5/02416; A61B 5/0245; A61B 5/0456;
(Continued)

(56) References Cited

U.S. PATENT DOCUMENTS

| | | |
|---|---|---|
| 6,381,559 B1 | 4/2002 | Huang |
| 2010/0125213 A1 | 5/2010 | Lo et al. |

(Continued)

FOREIGN PATENT DOCUMENTS

| | | |
|---|---|---|
| CN | 102018503 A | 4/2011 |
| CN | 105796079 A | 7/2016 |

(Continued)

OTHER PUBLICATIONS

International Search Report & Written Opinion dated Jan. 25, 2018, regarding PCT/CN2017/083055.
(Continued)

*Primary Examiner* — Mark D Remaly
(74) *Attorney, Agent, or Firm* — Intellectual Valley Law, P.C.

(57) ABSTRACT

The present application discloses an apparatus for determining a blood pressure of a subject. The apparatus includes one or more sensors configured to measure a first physiological parameter of the subject; a memory; and one or more processors. The memory stores computer-executable instructions for controlling the one or more processors to decompose a first physiological signal corresponding to the first physiological parameter using an empirical mode decomposition algorithm into a sum of a plurality of intrinsic mode functions and a residual; identify one or more first intrinsic mode functions of the plurality of intrinsic mode functions that are associated with a noise signal, thereby obtaining one or more second intrinsic mode functions of the plurality of intrinsic mode functions that are different from the one or more first intrinsic mode functions; and calculate a denoised physiological signal by accumulating the one or more second intrinsic mode functions.

20 Claims, 6 Drawing Sheets

(52) U.S. Cl.
CPC .......... *A61B 5/0456* (2013.01); *A61B 5/7203* (2013.01); *A61B 5/7221* (2013.01); *A61B 5/02116* (2013.01); *A61B 5/7225* (2013.01); *A61B 5/7278* (2013.01)

(58) Field of Classification Search
CPC ... A61B 5/7203; A61B 5/7221; A61B 5/7225; A61B 5/7278
See application file for complete search history.

(56) References Cited

U.S. PATENT DOCUMENTS

| | | |
|---|---|---|
| 2011/0015532 A1 | 1/2011 | Koertge et al. |
| 2018/0075209 A1 | 3/2018 | Li |

FOREIGN PATENT DOCUMENTS

| | | | |
|---|---|---|---|
| CN | 106073729 | A | 11/2016 |
| CN | 106343976 | A | 1/2017 |
| GB | 2490594 | A | 11/2012 |
| JP | 2016209019 | A | 12/2016 |

OTHER PUBLICATIONS

Continuous Cuffless Blood Pressure Estimation Using Pulse Transit Time and Photoplethysmogram Intensity Ratio, Xiao-Rong Ding et al., IEEE Transactions on Biomedical Engineering, May 31, 2016, No. 5 vol. 63 Introduction and methodology.
Extended European Search Report in the European Patent Application No. 17866379.5, dated Nov. 13, 2020.

APPARATUS AND METHOD FOR DETERMINING A BLOOD PRESSURE OF A SUBJECT

CROSS-REFERENCE TO RELATED APPLICATION

This application is a national stage application under 35 U.S.C. § 371 of International Application No. PCT/CN2017/083055, filed May 4, 2017, the contents of which are incorporated by reference in the entirety.

TECHNICAL FIELD

The present invention relates to medical devices, more particularly, to an apparatus and a method for determining a blood pressure of a subject.

BACKGROUND

Conventional blood pressure measurement apparatuses include sphygmomanometer, oscillometry, and invasive vascular pressure monitor. Blood pressure measurement using a sphygmomanometer is based on Korotkoff sound. Typically, a sphygmomanometer includes a stethoscope and a cuff. Oscillometry includes a cuff and electronics to determine the blood pressure based on cuff pressure oscillations. The invasive vascular pressure monitoring method involves placing a cannula needle or catheter into an artery. These conventional methods are either invasive or cumbersome.

SUMMARY

In one aspect, the present invention provides an apparatus for determining a blood pressure of a subject, comprising one or more sensors configured to measure a first physiological parameter of the subject; a memory; and one or more processors; wherein the one or more sensors, the memory and the one or more processors are coupled to each other; the memory stores computer-executable instructions for controlling the one or more processors to decompose a first physiological signal corresponding to the first physiological parameter using an empirical mode decomposition algorithm into a sum of a plurality of intrinsic mode functions and a residual; identify one or more first intrinsic mode functions of the plurality of intrinsic mode functions that are associated with a noise signal, thereby obtaining one or more second intrinsic mode functions of the plurality of intrinsic mode functions that are different from the one or more first intrinsic mode functions; and calculate a denoised physiological signal by accumulating the one or more second intrinsic mode functions.

Optionally, each of the plurality of intrinsic mode functions has a characteristic frequency, values of characteristic frequencies of the plurality of intrinsic mode functions are different from each other.

Optionally, the memory stores computer-executable instructions for controlling the one or more processors to select one or more of the plurality of intrinsic mode functions having characteristic frequencies outside a range of acceptable characteristic frequencies as the one or more first intrinsic mode functions.

Optionally, the one or more first intrinsic mode functions are associated with low frequency baseline drifting.

Optionally, the one or more first intrinsic mode functions are associated with a high frequency noise.

Optionally, the memory stores computer-executable instructions for controlling the one or more processors to, prior to decompose a first physiological signal, filter a high frequency noise from a second physiological signal to obtain the first physiological signal.

Optionally, filter the high frequency noise is performed by mathematical morphology filtering.

Optionally, the first physiological parameter is a pulse wave; and the first physiological signal is a photoplethysmogram signal; the memory stores computer-executable instructions for controlling the one or more processors to calculate a ratio of a photoplethysmogram peak intensity to a photoplethysmogram valley intensity in one cardiac cycle; and determine a photoplethysmogram intensity ratio based on the ratio of the photoplethysmogram peak intensity to the photoplethysmogram valley intensity in the one cardiac cycle.

Optionally, the memory further stores computer-executable instructions for controlling the one or more processors to obtain a first electrocardiography R-wave signal; and determine a time interval between an electrocardiography R-wave peak of the first electrocardiography R-wave signal and a peak of a first derivative of the denoised physiological signal in one cardiac cycle; and determine a pulse transit time based on the time interval.

Optionally, the one or more sensors are configured to detect an electrocardiography R-wave of the subject to acquire a second electrocardiography R-wave signal; the memory stores computer-executable instructions for controlling the one or more processors to filter a high frequency noise from a second electrocardiography R-wave signal thereby obtaining the first electrocardiography R-wave signal.

Optionally, the memory stores computer-executable instructions for controlling the one or more processors to determine the blood pressure of the subject using a blood pressure calculation algorithm based on the pulse transit time and the photoplethysmogram intensity ratio.

Optionally, the memory stores computer-executable instructions for controlling the one or more processors to determine the blood pressure of the subject according to the following equations:

$$DBP = \frac{a}{PIR} + b\frac{m}{h^2} + c; \text{ and} \quad (1)$$

$$SBP = \frac{a}{PIR} + b\frac{m}{h^2} + \frac{d}{PTT^2} + e; \quad (2)$$

wherein DBP is a diastolic blood pressure of the subject, SBP is a systolic blood pressure of the subject, FIT is the pulse transit time, PIR is the photoplethysmogram intensity ratio, m is a body weight of the subject, h is a height of the subject, and a, b, c, d, and e are constant coefficients.

In another aspect, the present invention provides a method of determining a blood pressure of a subject, comprising decomposing a first physiological signal corresponding to a first physiological parameter using an empirical mode decomposition algorithm into a sum of a plurality of intrinsic mode functions and a residual; identifying one or more first intrinsic mode functions of the plurality of intrinsic mode functions that are associated with a noise signal, thereby obtaining one or more second intrinsic mode functions of the plurality of intrinsic mode functions that are different from the one or more first intrinsic mode functions;

and calculating a denoised physiological signal by accumulating the one or more second intrinsic mode functions.

Optionally, each of the plurality of intrinsic mode functions has a characteristic frequency, values of characteristic frequencies of the plurality of intrinsic mode functions are different from each other.

Optionally, identifying the one or more first intrinsic mode functions comprises selecting one or more of the plurality of intrinsic mode functions having characteristic frequencies outside a range of acceptable characteristic frequencies as the one or more first intrinsic mode functions.

Optionally, the one or more first intrinsic mode functions are associated with low frequency baseline drifting.

Optionally, the one or more first intrinsic mode functions are associated with a high frequency noise.

Optionally, prior to decomposing the first physiological signal, the method further comprises filtering a high frequency noise from a second physiological signal thereby obtaining the first physiological signal.

Optionally, filtering the high frequency noise is performed by mathematical morphology filtering.

Optionally, the first physiological parameter is a pulse wave; and the first physiological signal is a photoplethysmogram signal; the method further comprising calculating a ratio of a photoplethysmogram peak intensity to a photoplethysmogram valley intensity in one cardiac cycle; and determining a photoplethysmogram intensity ratio based on the ratio of the photoplethysmogram peak intensity to the photoplethysmogram valley intensity in the one cardiac cycle.

Optionally, the method further comprises obtaining a first electrocardiography R-wave signal of the subject; determining a time interval between an electrocardiography R-wave peak of the first electrocardiography R-wave signal and a peak of a first derivative of the denoised physiological signal in one cardiac cycle; and determining a pulse transit time based on the time interval.

Optionally, the method further comprises measuring an electrocardiography R-wave of the subject to obtain a second electrocardiography R-wave signal; and filtering a high frequency noise from a second electrocardiography R-wave signal thereby obtaining the first electrocardiography R-wave signal.

Optionally, the method further comprises determining the blood pressure of the subject using a blood pressure calculation algorithm based on the pulse transit time and the photoplethysmogram intensity ratio.

Optionally, the blood pressure of the subject is determined according to the following equations:

$$DBP = \frac{a}{PIR} + b\frac{m}{h^2} + c; \text{ and} \quad (1)$$

$$SBP = \frac{a}{PIR} + b\frac{m}{h^2} + \frac{d}{PTT^2} + e; \quad (2)$$

wherein DBP is a diastolic blood pressure of the subject, SBP is a systolic blood pressure of the subject, PTT is the pulse transit time, PIR is the photoplethysmogram intensity ratio, m is a body weight of the subject, h is a height of the subject, and a, b, c, d, and e are constant coefficients.

BRIEF DESCRIPTION OF THE FIGURES

The following drawings are merely examples for illustrative purposes according to various disclosed embodiments and are not intended to limit the scope of the present invention.

DETAILED DESCRIPTION

Figure 1:
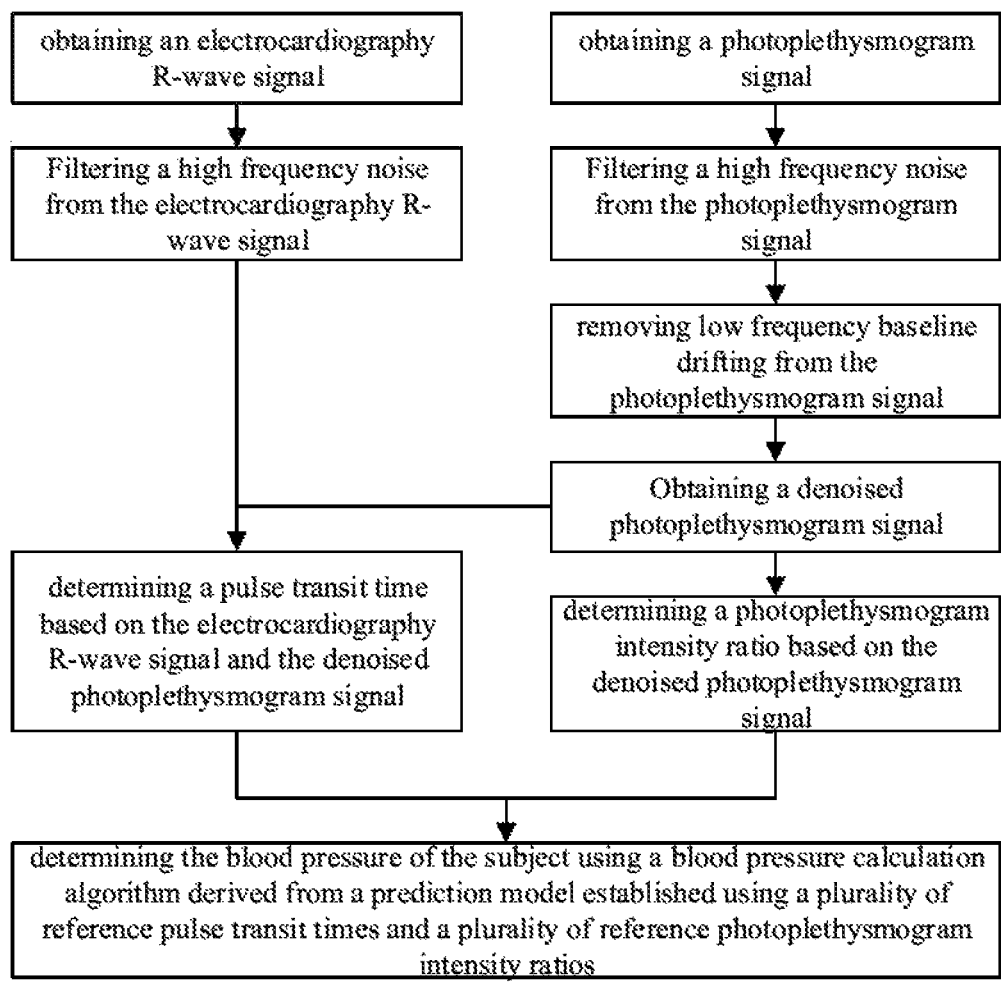
FIG. 1 is a flow chart illustrating a method of determining a blood pressure of a subject in some embodiments according to the present disclosure.

The disclosure will now be described more specifically with reference to the following embodiments. It is to be noted that the following descriptions of some embodiments are presented herein for purpose of illustration and description only. It is not intended to be exhaustive or to be limited to the precise form disclosed.

Non-invasive and cuff-less blood pressure measuring methods and apparatuses have become a focus of research and development in recent years. Conventional cuff-less and non-invasive blood pressure measuring apparatuses cannot accurately and reliably measure a subject's blood pressure, e.g., providing a blood pressure measurement comparable to that measured by sphygmomanometer and oscillometry. For example, some of these conventional cuff-less and non-invasive blood pressure measuring methods and apparatuses are based on photoplethysmogram signals and electrocardiography R-wave signals. These physiological signals, however, are relatively weak signals having a large noise background. Moreover, these signals are heavily affected by low frequency baseline drifting caused by, e.g., the subject's motion and respiratory activities, making it difficult to accurately determine characteristic points of the signal such as a wave peak, a wave valley, etc. Conventional denoising methods are not effective in removing these noises in the physiological signals. Further, the conventional cuff-less and non-invasive blood pressure measuring methods and apparatuses do not take into account the effects of vasomotor tone on the blood pressure, and the effects of body weight on the blood pressure.

Accordingly, the present disclosure provides, inter alia, an apparatus and a method for determining a blood pressure of a subject that substantially obviate one or more of the problems due to limitations and disadvantages of the related art. In one aspect, the present disclosure provides an apparatus for determining a blood pressure of a subject. In some embodiments, the apparatus includes one or more sensors configured to measure a first physiological parameter of the subject; a memory; and one or more processors. The one or more sensors, the memory and the one or more processors are coupled to each other. In some embodiments, the memory stores computer-executable instructions for controlling the one or more processors to decompose a first physiological signal corresponding to the first physiological parameter using an empirical mode decomposition algorithm into a sum of a plurality of intrinsic mode functions and a residual; identify one or more first intrinsic mode functions of the plurality of intrinsic mode functions that are associated with a noise signal, thereby obtaining one or more second intrinsic mode functions of the plurality of intrinsic mode functions that are different from the one or more first intrinsic mode functions; and calculate a denoised physiological signal by accumulating the one or more second intrinsic mode functions.

In another aspect, the present disclosure provides a method of determining a blood pressure of a subject. In some embodiments, the method includes decomposing a first physiological signal corresponding to a first physiological parameter using an empirical mode decomposition algorithm into a sum of a plurality of intrinsic mode functions and a residual; identifying one or more first intrinsic mode functions of the plurality of intrinsic mode functions that are associated with a noise signal, thereby obtaining one or more second intrinsic mode functions of the plurality of intrinsic mode functions that are different from the one or more first intrinsic mode functions; and calculating a denoised physiological signal by accumulating the one or more second intrinsic mode functions.

As used herein, the term "physiological signal" refers to a signal which is received from the one or more sensors, or a signal which is received from the one or more sensors and further processed by one or more data processing treatments such as filtering and denoising. As used herein, the term "physiological parameter" refers to any parameter that gives information about the health of a subject. Optionally, the physiological parameter refers to a parameter which may be extracted or otherwise obtained by analyzing the one or more physiological signals. Examples of physiological parameters include, but are not limited to, a blood pressure, a heart rate, and the like.

FIG. 1 is a flow chart illustrating a method of determining a blood pressure of a subject in some embodiments according to the present disclosure. Referring to FIG. 1, the method in some embodiments includes determining the blood pressure of the subject using a blood pressure calculation algorithm. In some embodiments, the blood pressure of the subject is calculated using the following equations:

$$DBP = \frac{a}{PIR} + b\frac{m}{h^2} + c; \text{ and} \quad (1)$$

$$SBP = \frac{a}{PIR} + b\frac{m}{h^2} + \frac{d}{PTT^2} + e; \quad (2)$$

wherein DBP is a diastolic blood pressure, SBP is a systolic blood pressure, PT is a pulse transit time, PIR is a photoplethysmogram intensity ratio, m is a body weight of the subject, h is a height of the subject, and a, b, c, d, and e are constant coefficients.

In some embodiments, the constant coefficients of the blood pressure calculation algorithm may be obtained by calibrating the pulse transit time and the photoplethysmogram intensity ratio with blood pressure values obtained using other reliable methods such as sphygmomanometer, oscillometry, invasive vascular pressure monitoring, or non-invasive blood pressure measuring methods. In some embodiments, the pulse transit time and the photoplethysmogram intensity ratio are calibrated with subject's own blood pressure data obtained using other reliable methods. In some embodiments, the constant coefficients may be first established for a plurality of groups of sub-populations, respectively. Each of the plurality of groups of sub-populations may have one or more common characteristic, e.g., age, gender, health condition, disease condition, treatment condition, height, weight, and body mass index. When applying the method to determine a subject's blood pressure, the subject may be first classified by the one or more common characteristics. The method further includes selecting a set of reference constant coefficients established for a plurality of subpopulations, respectively. A set of constant coefficients that best fits the subject is then chosen based on the classification, and is used for calculating the subject's blood pressure. Once the constant coefficients are determined, the subject's blood pressure may be calculated based on the pulse transit time and the photoplethysmogram intensity ratio.

Referring to FIG. 1, in some embodiments, the method further includes obtaining a denoised photoplethysmogram signal; and determining a photoplethysmogram intensity ratio based on the denoised photoplethysmogram signal. Noise signals in the photoplethysmogram signal includes low frequency baseline drifting and one or more high frequency noise signals. Low frequency baseline drifting is due to the subject's motion and respiratory activities. Examples of high frequency noise signals include random high frequency noises and power line interference noises due to environmental interference.

In some embodiments, one or more noises may be removed by first decomposing a first physiological signal corresponding to a first physiological parameter. Optionally, the first physiological parameter is a pulse wave; and the first physiological signal is a pulse wave signal (e.g., a photoplethysmogram signal). Optionally, the first physiological parameter is a heart rate, and the first physiological signal is an electrocardiography wave signal, e.g., an electrocardiography R-wave signal. Various other physiological signals may be denoised using the method described herein.

In some embodiments, the method includes decomposing a first physiological signal corresponding to a first physiological parameter using an empirical mode decomposition algorithm into a sum of a plurality of intrinsic mode functions and a residual. In one example, the first physiological signal may be decomposed into a function according to the following equation:

$$s(t) = \sum_{k=1}^{N} IMF_k(t) + r_N(t); \quad (3)$$

wherein s(t) is the first physiological signal; IMF stands for intrinsic mode functions; k is an integer, $1 \leq k \leq N$; N is an integer greater than 2; and $r_N(t)$ stands for a residual, which is a monotonic signal. Low frequency baseline drifting includes the residual and one or more intrinsic mode functions having low frequencies.

In some embodiments, the empirical mode decomposition process is a reiterating process that includes decomposing the first physiological signal multiple times to obtain a plurality of intrinsic mode functions and until a residual that does not include a wave signal is obtained by the reiterating process. Optionally, the empirical mode decomposition process includes identifying a maxima and a minima of the first physiological signal; calculating an upper envelop and a lower envelop based on the maxima and the minimal; and subtracting a mean of the upper envelop and the lower envelop from the first physiological signal to obtain a first mode of the plurality of intrinsic mode functions. Optionally, the empirical mode decomposition process further includes subtracting the first mode from the first physiological signal to obtain a first residual; identifying a maxima and a minima of the first residual; calculating an upper envelop and a lower envelop of the first residual based on the maxima and the minimal of the first residual; and subtracting a mean of the upper envelop and the lower envelop from the first residual to obtain a second mode of the plurality of intrinsic mode functions. Optionally, the empirical mode decomposition process further includes reiterating the above process to obtain the plurality of intrinsic mode functions, and a residual that does not include a wave signal and cannot be decomposed any more.

In some embodiments, each of the plurality of intrinsic mode functions has a characteristic frequency, values of characteristic frequencies of the plurality of intrinsic mode functions are different from each other. In one example, the first physiological signal is decomposed into IMF1, IMF2, IMF3, IMF4, IMF5, and a residual r. The frequencies of IMF1 to IMF5 decrease sequentially from IMF1 to IMF5, with IMF1 has the highest frequency and IMF5 has the lowest frequency.

In some embodiments, the method further includes identifying one or more first intrinsic mode functions of the plurality of intrinsic mode functions that are associated with a noise signal, thereby obtaining one or more second intrinsic mode functions of the plurality of intrinsic mode functions that are different from the one or more first intrinsic mode functions. Optionally, the step of identifying the one or more first intrinsic mode functions includes selecting one or more of the plurality of intrinsic mode functions having characteristic frequencies outside a range of acceptable characteristic frequencies as the one or more first intrinsic mode functions. Optionally, the range of acceptable characteristic frequencies is a range of characteristic frequencies corresponding to characteristic frequencies of the first physiological parameter. Optionally, the one or more second intrinsic mode functions of the plurality of intrinsic mode functions have characteristic frequencies in the range of acceptable characteristic frequencies. In one example, the first physiological parameter is a pulse wave, the first physiological signal is a pulse wave signal (e.g., a photoplethysmogram signal), and the range of acceptable characteristic frequencies corresponding to characteristic frequencies of the pulse wave (e.g., the pulse wave of an average adult) is approximately 0.8 to approximately 1.6 Hz. In one example, IMF1, IMF4, and IMF5 are first intrinsic mode functions having characteristic frequencies outside the range of acceptable characteristic frequencies of the pulse wave, and IMF2 and IMF3 are second intrinsic mode functions having characteristic frequencies different from the first intrinsic mode functions, e.g., the characteristic frequencies of IMF2 and IMF3 are in the range of the characteristic frequencies corresponding to the pulse wave. In one example, IMF4 and IMF5 correspond to low frequency baseline drifting, and IMF1 corresponds to a high frequency noise signal. By decomposing the first physiological signal and isolating the low frequency baseline drifting, the low frequency baseline drifting can be removed from the first physiological signal, e.g., denoised. Similarly, by decomposing the first physiological signal and isolating the high frequency noise signal, the high frequency noise signal can be removed from the first physiological signal.

In another example, high frequency noise signals are removed prior to the empirical mode decomposition process. Thus, the decomposing process produces one or more intrinsic mode functions corresponding to the low frequency baseline drifting, but not intrinsic mode functions corresponding to the high frequency noise signals. Accordingly, the method includes removing the low frequency baseline drifting from the first physiological signal by the empirical mode decomposition process.

In some embodiments, the method further includes calculating a denoised physiological signal by accumulating the one or more second intrinsic mode functions. Optionally, the denoised physiological signal may be expressed using the following equation:

$$ds(t)=\Sigma_{k=m}^{n}IMF_k(t) \quad (4);$$

wherein ds(t) stands for the denoised physiological signal; k is an integer; m≤k≤n, m is an integer greater than or equal to 1; n is an integer less than N, and greater than or equal to m. Optionally, $IMF_{n+1}(t)$ to $IMF_N(t)$ corresponds to the low frequency baseline drifting. Optionally, $IMF_1(t)$ to $IMF_{m-1}(t)$ corresponds to the high frequency noise signals.

In some embodiments, the intrinsic mode functions having the lowest characteristic frequencies, $IMF_{n+1}$ to $IMF_N$, and the residual, $r_N(t)$, are not used in computing the denoised physiological signal. Optionally, the denoised physiological signal may be expressed using the following equation:

$$ds(t)=\Sigma_{k=1}^{n}IMF_k(t) \quad (5);$$

wherein ds(t) stands for the denoised physiological signal; k is an integer; 1≤k≤n, n is an integer less than N, and greater than or equal to 1. Optionally, $IMF_{n+1}(t)$ to $IMF_N(t)$ corresponds to the low frequency baseline drifting.

In some embodiments, the intrinsic mode function having the lowest characteristic frequency, $IMF_N$, and the residual, $r_N(t)$, are not used in computing the denoised physiological signal. Optionally, the denoised physiological signal may be expressed using the following equation:

$$ds(t)=\Sigma_{k=1}^{N-1}IMF_k(t) \quad (6);$$

wherein ds(t) stands for the denoised physiological signal; k is an integer, 1≤k—≤N−1; and N is an integer greater than 2.

In some embodiments, the first physiological parameter is a pulse wave; and the first physiological signal is a pulse wave signal (e.g., a photoplethysmogram signal). Optionally, the denoised pulse wave signal (e.g., a denoised photoplethysmogram signal) may be expressed using the following equation:

$$PPG=\Sigma_{k=m}^{n}IMF_k(t) \quad (7);$$

wherein PPG stands for the denoised photoplethysmogram signal; k is an integer, 1≤k≤N−1; and N is an integer greater than 2.

In some embodiments, the intrinsic mode functions having the lowest characteristic frequencies, $IMF_{n+1}$ to $IMF_N$, and the residual, $r_N(t)$, are not used in computing the denoised photoplethysmogram signal. Optionally, the denoised pulse wave signal (e.g., a denoised photoplethysmogram signal) may be expressed using the following equation:

$$PPG=\Sigma_{k=1}^{n}IMF_k(t) \quad (8);$$

wherein PPG stands for the denoised photoplethysmogram signal; k is an integer, $1 \leq k \leq n$; and n is an integer less than N, and greater than or equal to 1. Optionally, $IMF_{n+1}(t)$ to $IMF_N(t)$ corresponds to the low frequency baseline drifting.

In some embodiments, the intrinsic mode function having the lowest characteristic frequency, $IMF_N$, and the residual, $r_N(t)$, are not used in computing the denoised photoplethysmogram signal. Optionally, the denoised pulse wave signal (e.g., a denoised photoplethysmogram signal) may be expressed using the following equation:

$$PPG = \Sigma_{k=1}^{N-1} IMF_k(t) \tag{9};$$

wherein PPG stands for the denoised photoplethysmogram signal; k is an integer, $1 \leq k \leq N-1$; and N is an integer greater than 2.

Figure 2:
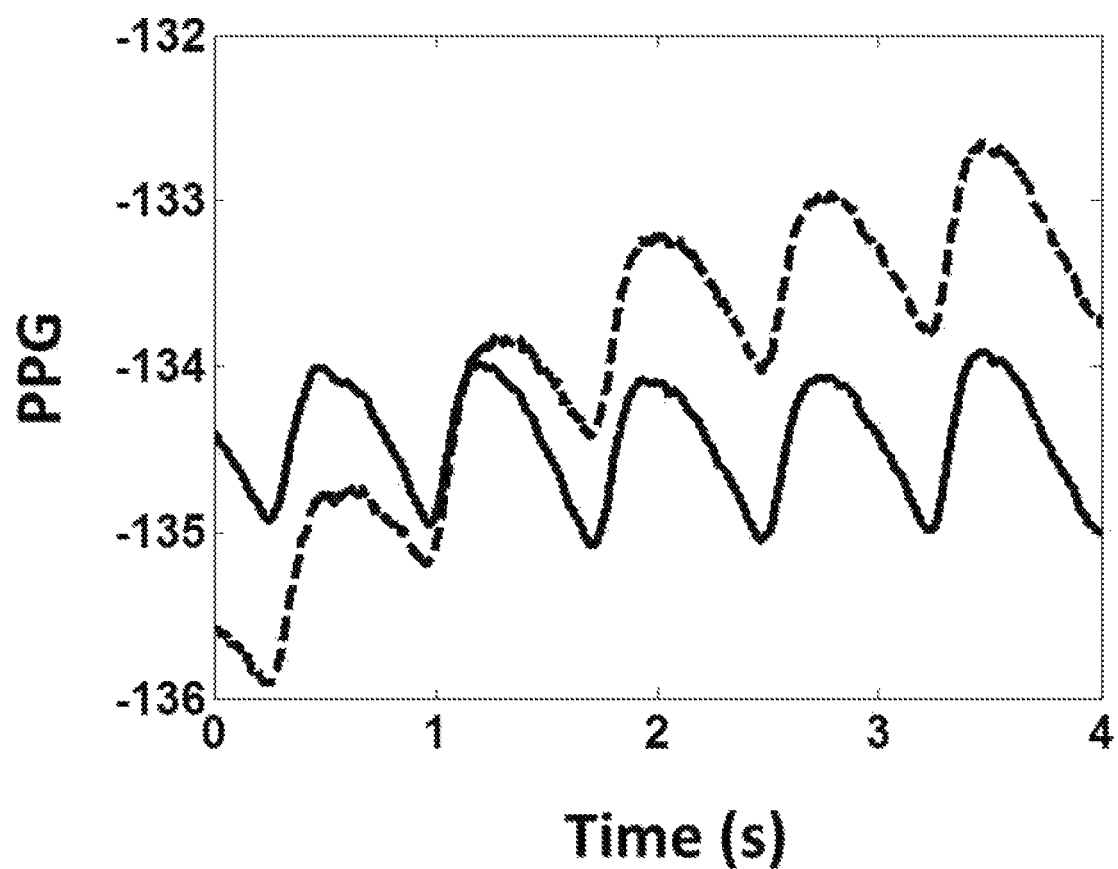
FIG. 2 is a comparison between a photoplethysmogram signal prior to the denoising process (the dotted line) and the photoplethysmogram signal subsequent to the denoising process (the solid line) in some embodiments according to the present disclosure.

FIG. 2 is a comparison between a photoplethysmogram signal prior to the denoising process (the dotted line) and the photoplethysmogram signal subsequent to the denoising process (the solid line) in some embodiments according to the present disclosure. Referring to FIG. 2, the low frequency baseline drifting is removed in the photoplethysmogram signal subsequent to the denoising process.

Referring to FIG. 1, prior to decomposing the first physiological signal, the method further includes filtering a high frequency noise from a second physiological signal thereby obtaining the first physiological signal. Optionally, prior to the filtering the high frequency noise from the second physiological signal, the method further includes measuring the second physiological signal corresponding to the first physiological parameter. Optionally, the second physiological signal is a raw (e.g., unprocessed) data of the first physiological parameter. In one example, the first physiological parameter is a pulse wave, the second physiological signal is an unprocessed pulse wave signal (e.g., an unprocessed photoplethysmogram signal), and the first physiological signal is a pulse wave signal (e.g., a photoplethysmogram signal) in which a high frequency noise is removed.

In some embodiments, the step of filtering the high frequency noise is performed by mathematical morphology filtering. Optionally, the step of filtering the high frequency noise is performed using a Savitzky-Golay FIR filter, e.g., a third derivative Savitzky-Golay FIR filter.

Figure 3:
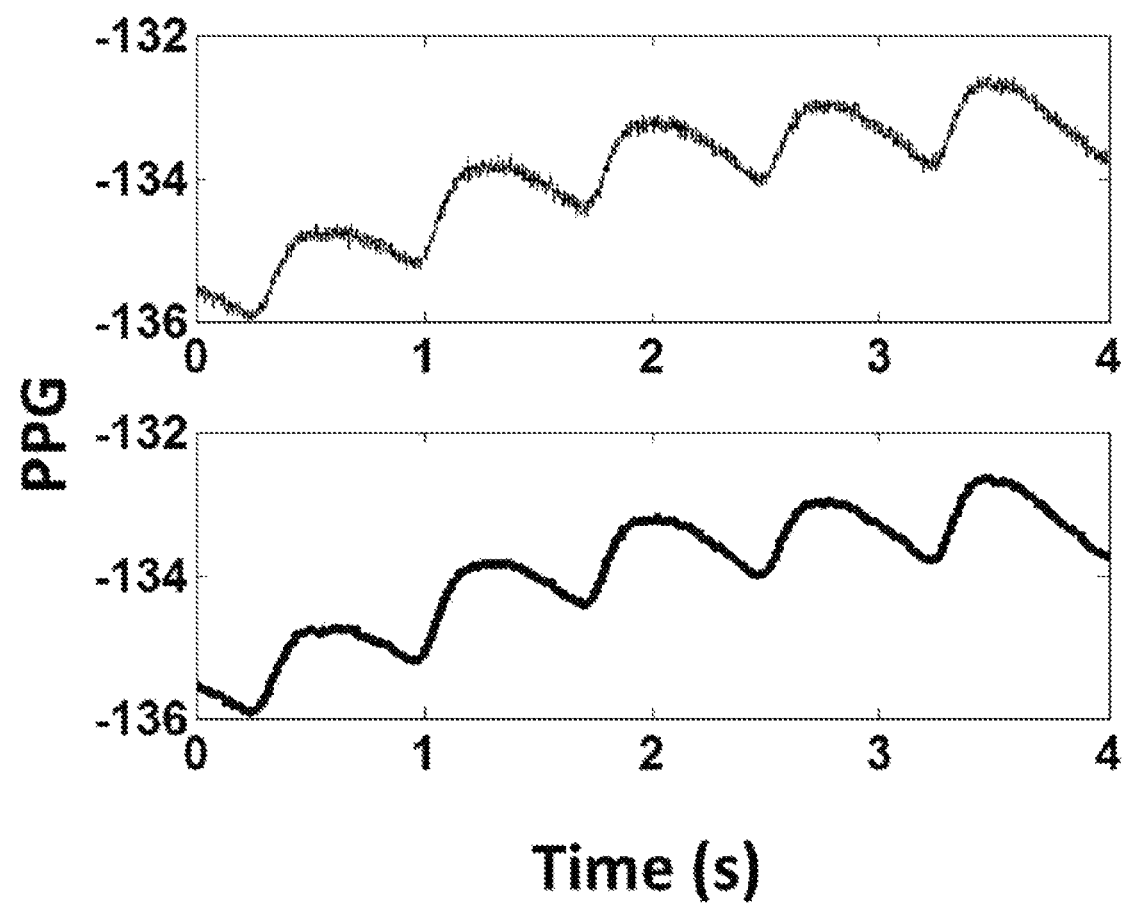
FIG. 3 is a comparison between a photoplethysmogram signal prior to the filtering process (top panel) and the photoplethysmogram signal subsequent to the filtering process (bottom panel) in some embodiments according to the present disclosure.

FIG. 3 is a comparison between a photoplethysmogram signal prior to the filtering process (top panel) and the photoplethysmogram signal subsequent to the filtering process (bottom panel) in some embodiments according to the present disclosure. Referring to FIG. 3, the high frequency noises in the photoplethysmogram signal are removed subsequent to the filtering process. The photoplethysmogram signal is smoothed after the treatment by the Savitzky-Golay FIR filter.

Referring to FIG. 1, the method in some embodiments further includes obtaining a first electrocardiography R-wave signal of the subject for the purpose of determining a pulse transit time based on the first electrocardiography R-wave signal and the denoised physiological signal. Optionally, the method includes measuring an electrocardiography R-wave of the subject to obtain a second electrocardiography R-wave signal; and filtering a high frequency noise from a second electrocardiography R-wave signal thereby obtaining the first electrocardiography R-wave signal.

In some embodiments, the step of filtering the high frequency noise from the second electrocardiography R-wave signal is performed by mathematical morphology filtering. Optionally, the step of filtering the high frequency noise is performed using a Savitzky-Golay FIR filter, e.g., a third derivative Savitzky-Golay FIR filter.

Figure 4:
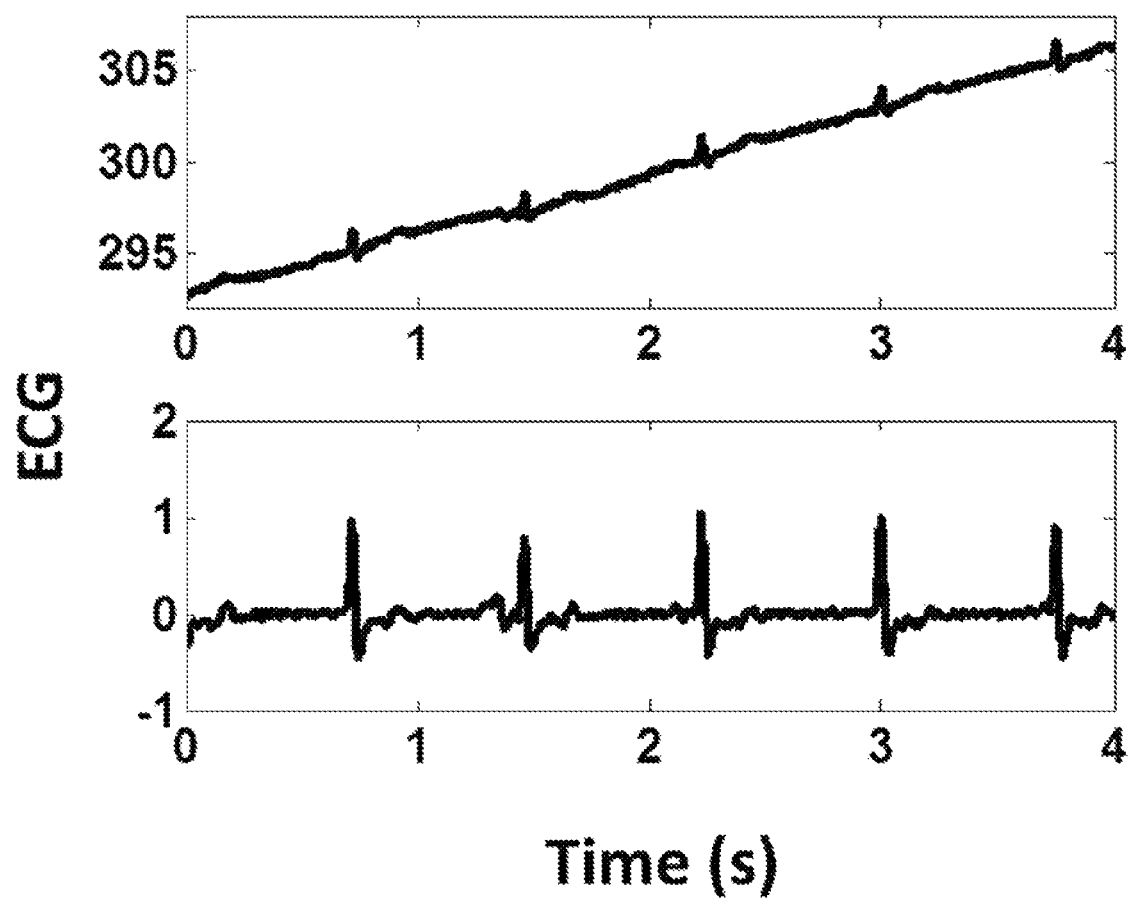
FIG. 4 is a comparison between an electrocardiography R-wave signal prior to the filtering process (top panel) and the electrocardiography R-wave signal subsequent to the filtering process (bottom panel) in some embodiments according to the present disclosure.

FIG. 4 is a comparison between an electrocardiography R-wave signal prior to the filtering process (top panel) and the electrocardiography R-wave signal subsequent to the filtering process (bottom panel) in some embodiments according to the present disclosure. Referring to FIG. 4, the high frequency noises in the electrocardiography R-wave signal are removed subsequent to the filtering process.

In some embodiments, the step of filtering the high frequency noise from the second electrocardiography R-wave signal is performed by the empirical mode decomposition described herein. Optionally, the step of filtering the high frequency noise from the second electrocardiography R-wave signal includes decomposing the second electrocardiography R-wave signal using an empirical mode decomposition algorithm into a sum of a plurality of intrinsic mode functions and a residual; identifying one or more first intrinsic mode functions of the plurality of intrinsic mode functions that are associated with a noise signal (e.g., a high frequency noise), thereby obtaining one or more second intrinsic mode functions of the plurality of intrinsic mode functions that are different from the one or more first intrinsic mode functions; and calculating a denoised electrocardiography R-wave signal (e.g., the first electrocardiography R-wave signal) by accumulating the one or more second intrinsic mode functions.

Referring to FIG. 1, once the first electrocardiography R-wave signal and the denoised photoplethysmogram signal are calculated, the method further includes determining a photoplethysmogram intensity ratio based on the denoised photoplethysmogram signal; and determining a pulse transit time based on the first electrocardiography R-wave signal and the denoised physiological signal. Optionally, the method further includes identifying characteristic points of the denoised photoplethysmogram signal and characteristic points of the first electrocardiography R-wave signal.

Figure 5:
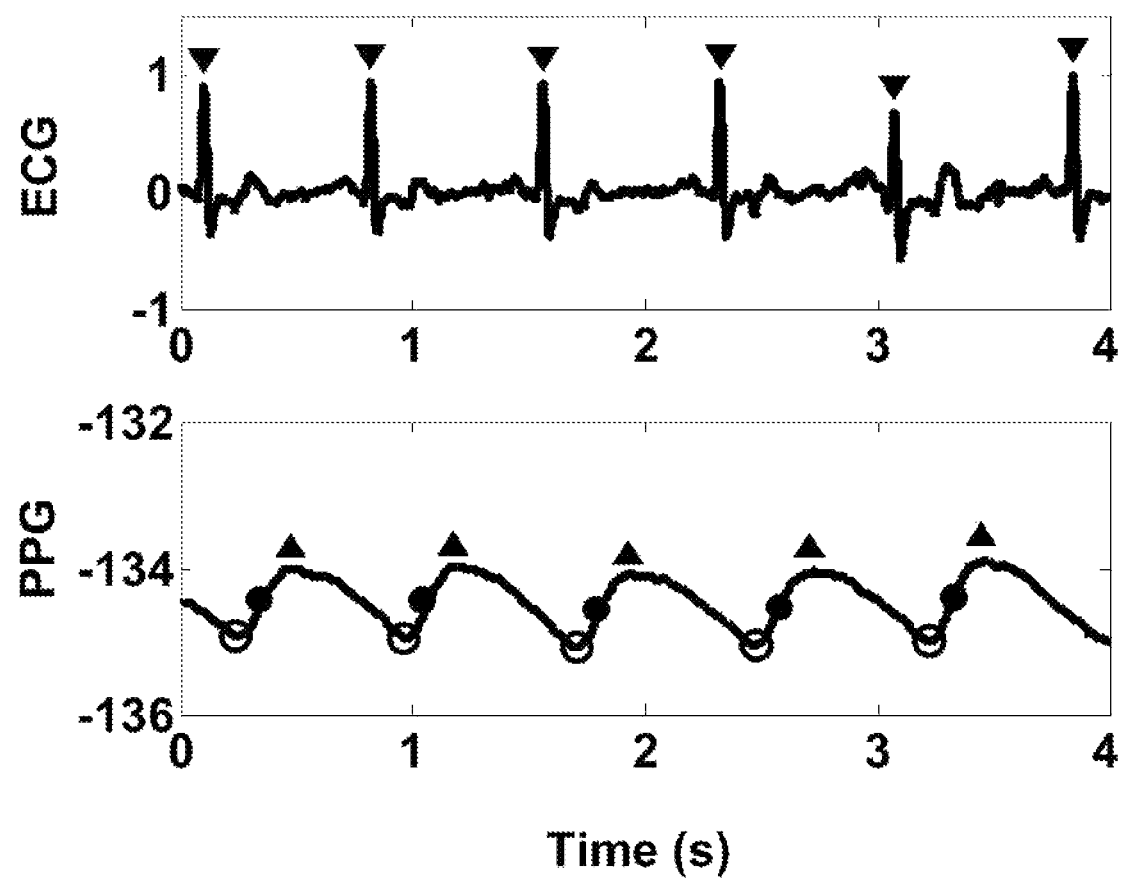
FIG. 5 is a diagram illustrating characteristic points of the denoised photoplethysmogram signal (PPG) and characteristic points of the first electrocardiography R-wave signal (ECO).

FIG. 5 is a diagram illustrating characteristic points of the denoised photoplethysmogram signal (PPG) and characteristic points of the first electrocardiography R-wave signal (ECG). Referring to FIG. 5, ▼ denotes an electrocardiography R-wave peak of the first electrocardiography R-wave signal in each cardiac cycle. As shown in FIG. 5, ▲ denotes a photoplethysmogram peak of the denoised photoplethysmogram signal in each cardiac cycle; ○ denotes a photoplethysmogram valley of the denoised photoplethysmogram signal in each cardiac cycle; and • denotes a peak of a first derivative of the denoised photoplethysmogram signal in each cardiac cycle.

Figure 6:
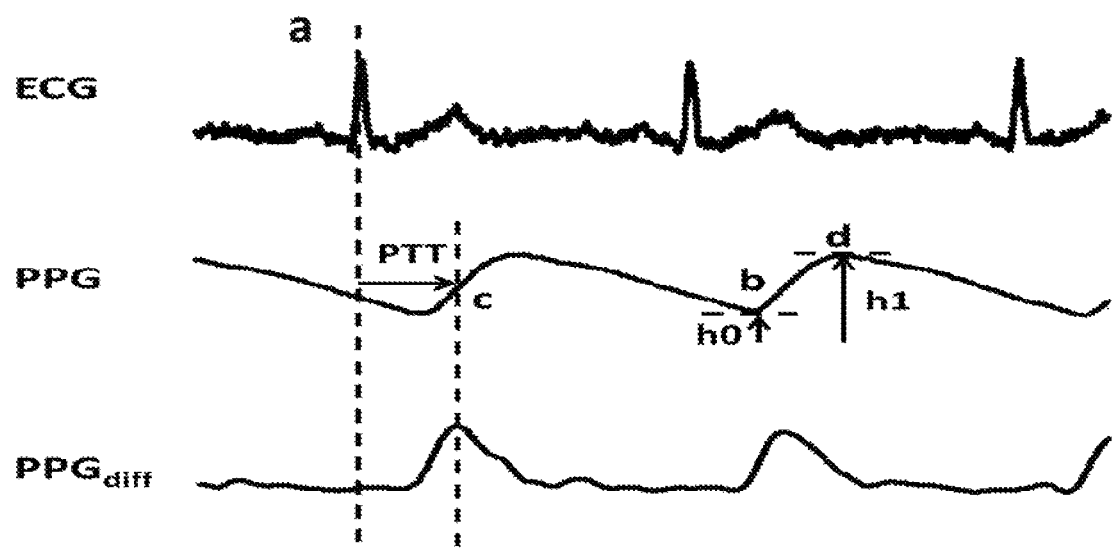
FIG. 6 illustrates a method of determining a pulse transit time (PTT) and determining a photoplethysmogram intensity ratio.

In some embodiments, the step of determining the photoplethysmogram intensity ratio includes calculating a ratio of a photoplethysmogram peak intensity to a photoplethysmogram valley intensity in one cardiac cycle. FIG. 6 illustrates a method of determining a pulse transit time (PIT) and determining a photoplethysmogram intensity ratio. Referring to FIG. 6, $h_1$ denotes a photoplethysmogram peak intensity of a photoplethysmogram peak d of the denoised photoplethysmogram signal in one cardiac cycle; and $h_0$ denotes a photoplethysmogram valley intensity of a photoplethysmogram valley b of the denoised photoplethysmogram signal in one cardiac cycle. The photoplethysmogram intensity ratio may be calculated based on the following equation:

$$PIR = \frac{h_1}{h_0}; \tag{10}$$

wherein PIR stands for the photoplethysmogram intensity ratio; $h_0$ stands for a photoplethysmogram valley intensity of a photoplethysnmogram valley of the denoised photoplethysmogram signal in one cardiac cycle; and $h_1$ stands for a photoplethysmogram peak intensity of a photoplethysmogram peak of the denoised photoplethysmogram signal in the one cardiac cycle.

In some embodiments, the step of determining the pulse transit time includes determining a time interval between an electrocardiography R-wave peak of the first electrocardiography R-wave signal and a peak of a first derivative of the denoised physiological signal in one cardiac cycle. Referring to FIG. 6, $PPG_{diff}$ is a first derivative of the denoised physiological signal. As shown in FIG. 6, point c in one cardiac cycle of the denoised physiological signal corresponds to a peak of a first derivative of the denoised physiological signal in the same cardiac cycle, and point a of the first electrocardiography R-wave signal corresponds to an electrocardiography R-wave peak in the same cardiac cycle. The pulse transit time is determined as the time difference between point a and point c, i.e., the time interval between the electrocardiography R-wave peak of the first electrocardiography R-wave signal and the peak of the first derivative of the denoised physiological signal in a same cardiac cycle.

Once the pulse transit time and the photoplethysmogram intensity ratio are determined, the blood pressure of the subject can be determined using a blood pressure calculation algorithm, as discussed above.

In some embodiments, the method includes acquiring an electrocardiography R-wave signal and acquiring an arterial pulse wave signal, e.g., a radial arterial pulse wave signal.

Figure 7:
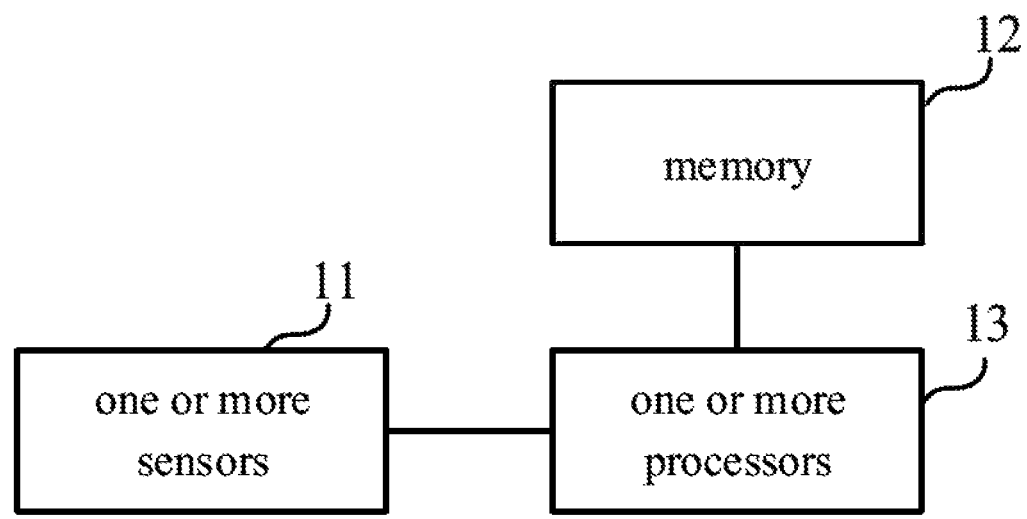
FIG. 7 is a schematic diagram illustrating the structure of an apparatus for determining a blood pressure of a subject in some embodiments according to the present disclosure.

In another aspect, the present disclosure provides an apparatus for determining a blood pressure of a subject. FIG. 7 is a schematic diagram illustrating the structure of an apparatus for determining a blood pressure of a subject in some embodiments according to the present disclosure. Referring to FIG. 7, the apparatus in some embodiments includes one or more sensors 11, a memory 12, and one or more processors 13. The one or more sensors 11 are configured to acquire one or more physiological signals of the subject. Examples of physiological signals include both electrical signals and non-electrical signals. Examples of electrical signals include, but are not limited to, an electrocardiogram signal, an electroencephalogram signal, an electromyogram signal, and the like. Examples of non-electrical biometric signals include, but are not limited to, a blood pressure signal, a pulse wave signal, a body temperature signal, a body motion signal, and the like. Optionally, the one or more physiological signals includes at least a pulse wave signal (e.g., a photoplethysmogram signal) of the subject. Optionally, the one or more physiological signals includes at least a heart rate signal (e.g., an electrocardiography wave signal) of the subject. Examples of biosensors include, but are not limited to, a photoelectric sensor, a pressure sensor, an accelerometer, barometer, and an image sensor.

Optionally, the apparatus is a wearable apparatus. Optionally, the apparatus is integrated into a smart phone. Optionally, the apparatus is integrated into a tablet computer. Optionally, the apparatus is a stand-alone apparatus.

In some embodiments, the memory 12 stores computer-executable instructions for controlling the one or more processors 13 to determine the blood pressure of the subject using a blood pressure calculation algorithm. Optionally, the blood pressure calculation algorithm is based on a pulse transit time and a photoplethysmogram intensity ratio of the subject. Optionally, the blood pressure of the subject is calculated using Equations (1) and (2) discussed above.

In some embodiments, the memory 12 stores computer-executable instructions for controlling the one or more processors 13 to first decompose a first physiological signal corresponding to a first physiological parameter. Optionally, the first physiological parameter is a pulse wave; and the first physiological signal is a pulse wave signal (e.g., a photoplethysmogram signal). Optionally, the first physiological parameter is a heart rate, and the first physiological signal is an electrocardiography wave signal, e.g., an electrocardiography R-wave signal. Various other physiological signals may be denoised using the apparatus described herein.

In some embodiments, the memory 12 stores computer-executable instructions for controlling the one or more processors 13 to first decompose a first physiological signal corresponding to a first physiological parameter using an empirical mode decomposition algorithm into a sum of a plurality of intrinsic mode functions and a residual. In one example, the first physiological signal may be decomposed into a function according to Equation (3) discussed above.

In some embodiments, each of the plurality of intrinsic mode functions has a characteristic frequency, values of characteristic frequencies of the plurality of intrinsic mode functions are different from each other. In some embodiments, the memory 12 stores computer-executable instructions for controlling the one or more processors 13 to identify one or more first intrinsic mode functions of the plurality of intrinsic mode functions that are associated with a noise signal, thereby obtaining and one or more second intrinsic mode functions of the plurality of intrinsic mode functions that are different from the one or more first intrinsic mode functions. Optionally, the memory 12 stores computer-executable instructions for controlling the one or more processors 13 to select one or more of the plurality of intrinsic mode functions having characteristic frequencies outside a range of acceptable characteristic frequencies as the one or more first intrinsic mode functions. Optionally, the one or more second intrinsic mode functions of the plurality of intrinsic mode functions have characteristic frequencies in the range of acceptable characteristic frequencies. Optionally, the range of acceptable characteristic frequencies is a range of characteristic frequencies corresponding to characteristic frequencies of the first physiological parameter. In one example, the first physiological parameter is a pulse wave, the first physiological signal is a pulse wave signal (e.g., a photoplethysmogram signal), and the range of acceptable characteristic frequencies corresponding to characteristic frequencies of the pulse wave (e.g., the pulse wave of an average adult) is approximately 0.8 to approximately 1.6 Hz. By decomposing the first physiological signal and isolating the low frequency baseline drifting, the low frequency baseline drifting can be removed from the first physiological signal, e.g., denoised. Similarly, by decomposing the first physiological signal and isolating the high frequency noise signal, the high frequency noise signal can be removed from the first physiological signal.

In some embodiments, the memory 12 stores computer-executable instructions for controlling the one or more processors 13 to calculate a denoised physiological signal by accumulating the one or more second intrinsic mode functions. Optionally, the denoised physiological signal may be expressed using Equation (4) discussed above. In some embodiments, the intrinsic mode functions having the lowest characteristic frequencies, $IMF_{n+1}$ to $IMF_N$, and the residual, $r_N(t)$, are not used in computing the denoised physiological signal. Optionally, the denoised physiological signal may be expressed using Equation (5) discussed above. In some embodiments, the intrinsic mode function having the lowest caracteristic frequency, $IMF_N$, and the residual, $r_N(t)$, are not used in computing the denoised physiological signal. Optionally, the denoised physiological signal may be expressed using Equation (6) discussed above. In some embodiments, the first physiological parameter is a pulse wave; and the first physiological signal is a pulse wave signal (e.g., a photoplethysmogram signal). Optionally, the denoised pulse wave signal (e.g., a denoised photoplethysmogram signal) may be expressed using Equation (7) discussed above. In some embodiments, the intrinsic mode functions having the lowest characteristic frequencies, $IMF_{n+1}$ to $IMF_N$, and the residual, $r_N(t)$, are not used in computing the denoised photoplethysmogram signal. Optionally, the denoised pulse wave signal (e.g., a denoised photoplethysmogram signal) may be expressed using Equation (8) discussed above. In some embodiments, the intrinsic mode function having the lowest characteristic frequency, $IMF_N$, and the residual, $r_N(t)$, are not used in computing the denoised photoplethysmogram signal. Optionally, the denoised pulse wave signal (e.g., a denoised photoplethysmogram signal) may be expressed using Equation (9) discussed above.

In some embodiments, the memory 12 stores computer-executable instructions for controlling the one or more processors 13 to, prior to decompose the first physiological signal, filter a high frequency noise from a second physiological signal thereby obtaining the first physiological signal. Optionally, prior to decompose the first physiological signal, the one or more sensors 11 are configured to acquire the second physiological signal corresponding to the first physiological parameter. Optionally, the second physiological signal is a raw (e.g., unprocessed) data of the first physiological parameter. In one example, the first physiological parameter is a pulse wave, the second physiological signal is an unprocessed pulse wave signal (e.g., an unprocessed photoplethysmogram signal), and the first physiological signal is a pulse wave signal (e.g., a photoplethysmogram signal) in which a high frequency noise is removed. Optionally, filtering the high frequency noise is performed by mathematical morphology filtering. Optionally, filter the high frequency noise is performed using a Savitzky-Golay FIR filter, e.g., a third derivative Savitzky-Golay FIR filter.

In some embodiments, the memory 12 stores computer-executable instructions for controlling the one or more processors 13 to obtain a first electrocardiography R-wave signal of the subject for the purpose of determining a pulse transit time based on the first electrocardiography R-wave signal and the denoised physiological signal. Optionally, the one or more sensors are configured to acquire an electrocardiography R-wave of the subject to obtain a second electrocardiography R-wave signal; and the memory 12 stores computer-executable instructions for controlling the one or more processors 13 to filter a high frequency noise from a second electrocardiography R-wave signal thereby obtaining the first electrocardiography R-wave signal. Optionally, filter the high frequency noise is performed by mathematical morphology filtering. Optionally, filter the high frequency noise is performed using a Savitzky-Golay FIR filter, e.g., a third derivative Savitzky-Golay FIR filter.

In some embodiments, the memory 12 stores computer-executable instructions for controlling the one or more processors 13 to filter the high frequency noise from the second electrocardiography R-wave signal by the empirical mode decomposition algorithm described herein. Optionally, the memory 12 stores computer-executable instructions for controlling the one or more processors 13 to decompose the second electrocardiography R-wave signal using an empirical mode decomposition algorithm into a sum of a plurality of intrinsic mode functions and a residual; identify one or more first intrinsic mode functions of the plurality of intrinsic mode functions that are associated with a noise signal (e.g., a high frequency noise), thereby obtaining one or more second intrinsic mode functions of the plurality of intrinsic mode functions that are different from the one or more first intrinsic mode functions; and calculate a denoised electrocardiography R-wave signal (e.g., the first electrocardiography R-wave signal) by accumulating the one or more second intrinsic mode functions.

In some embodiments, the first physiological parameter is a pulse wave; and the first physiological signal is a photoplethysmogram signal; the memory 12 stores computer-executable instructions for controlling the one or more processors 13 to determine a photoplethysmogram intensity ratio based on the denoised photoplethysmogram signal; and determine a pulse transit time based on the first electrocardiography R-wave signal and the denoised physiological signal. Optionally, the memory 12 stores computer-executable instructions for controlling the one or more processors 13 to identify characteristic points of the denoised photoplethysmogram signal and characteristic points of the first electrocardiography R-wave signal.

In some embodiments, the memory 12 stores computer-executable instructions for controlling the one or more processors 13 to calculate a ratio of a photoplethysmogram peak intensity to a photoplethysmogram valley intensity in one cardiac cycle, thereby determining the photoplethysmogram intensity ratio. Optionally, the photoplethysmogram intensity ratio is calculated based on Equation (10) discussed above.

In some embodiments, the memory 12 stores computer-executable instructions for controlling the one or more processors 13 to determine a time interval between an electrocardiography R-wave peak of the first electrocardiography R-wave signal and a peak of a first derivative of the denoised physiological signal in one cardiac cycle, thereby determining the pulse transit time.

In some embodiments, the apparatus further includes a data converter such as an analog-to-digital converter for converting the physiological signal measured by the one or more sensors 11 into digital data, and transmitting the digital data to the one or more processors 13 for analysis.

In some embodiments, the apparatus further includes a user interface for displaying information on a display and for the user to input data to the apparatus through an input device. The user may input data related to a subject's height, weight, and other physical parameters and genetic traits, and historical physiological parameter data (e.g., historical pulse wave data or historical heart rate data) of the subject.

Optionally, the one or more sensors 11 includes one or more electrocardiography sensors configured to acquire an electrocardiography R-wave signal and one or more pulse wave sensors such as a photoplethysmography sensor configured to acquire an arterial pulse wave signal, e.g., a radial arterial pulse wave signal. Optionally, the sensor for measuring electrocardiography R-wave includes a plurality of electrocardiography electrodes. Optionally, all sensors are integrated into the apparatus. Optionally, at least one sensor may be separate from the apparatus's main body and is in remote communication with (e.g., via wireless connection) the processor in the apparatus's main body. Optionally, the main body of the apparatus may be worn on one location of a subject (e.g., the wrist of the subject), and another sensor may be placed on an arterial site away from the main body (e.g., on the subject's leg).

In some embodiments, the apparatus includes a wireless transceiver for receiving or transmitting information from or to a remote site. For example, the apparatus may receive real-time database updates through the wireless transceiver.

Optionally, the subject is a human. Optionally, the subject is a mammal. Optionally, the subject is a pet (e.g., a dog, a cat).

Various appropriate memory may be used in the present apparatus. Examples of appropriate computer readable memories include, but are not limited to, magnetic disk or tape, optical storage media such as compact disk (CD) or DVD (digital versatile disk), flash memory, and other non-transitory media. Optionally, the memory is a non-transitory memory.

The foregoing description of the embodiments of the invention has been presented for purposes of illustration and description. It is not intended to be exhaustive or to limit the invention to the precise form or to exemplary embodiments disclosed. Accordingly, the foregoing description should be regarded as illustrative rather than restrictive. Obviously, many modifications and variations will be apparent to practitioners skilled in this art. The embodiments are chosen and described in order to explain the principles of the invention and its best mode practical application, thereby to enable persons skilled in the art to understand the invention for various embodiments and with various modifications as are suited to the particular use or implementation contemplated. It is intended that the scope of the invention be defined by the claims appended hereto and their equivalents in which all terms are meant in their broadest reasonable sense unless otherwise indicated. Therefore, the term "the invention", "the present invention" or the like does not necessarily limit the claim scope to a specific embodiment, and the reference to exemplary embodiments of the invention does not imply a limitation on the invention, and no such limitation is to be inferred. The invention is limited only by the spirit and scope of the appended claims. Moreover, these claims may refer to use "first", "second", etc. following with noun or element. Such terms should be understood as a nomenclature and should not be construed as giving the limitation on the number of the elements modified by such nomenclature unless specific number has been given. Any advantages and benefits described may not apply to all embodiments of the invention. It should be appreciated that variations may be made in the embodiments described by persons skilled in the art without departing from the scope of the present invention as defined by the following claims. Moreover, no element and component in the present disclosure is intended to be dedicated to the public regardless of whether the element or component is explicitly recited in the following claims.

What is claimed is:

1. An apparatus for determining a blood pressure of a subject, comprising:
   one or more sensors configured to measure a first physiological parameter of the subject;
   a memory; and
   one or more processors;
   wherein the one or more sensors, the memory and the one or more processors are coupled to each other;
   the memory stores computer-executable instructions for controlling the one or more processors to:
   decompose a first physiological signal corresponding to the first physiological parameter using an empirical mode decomposition algorithm into a sum of a plurality of intrinsic mode functions and a residual, wherein the first physiological parameter is a pulse wave; and the first physiological signal is a photoplethysmogram signal;
   identify one or more first intrinsic mode functions of the plurality of intrinsic mode functions that are associated with a noise signal, thereby obtaining one or more second intrinsic mode functions of the plurality of intrinsic mode functions that are different from the one or more first intrinsic mode functions;
   calculate a denoised physiological signal by accumulating the one or more second intrinsic mode functions;
   calculate a ratio of a photoplethysmogram peak intensity to a photoplethysmogram valley intensity in one cardiac cycle;
   determine a photoplethysmogram intensity ratio based on the ratio of the photoplethysmogram peak intensity to the photoplethysmogram valley intensity in the one cardiac cycle;
   obtain a first electrocardiography R-wave signal;
   determine a time interval between an electrocardiography R-wave peak of the first electrocardiography R-wave signal and a peak of a first derivative of the denoised physiological signal in one cardiac cycle;
   determine a pulse transit time based on the time interval; and
   determine the blood pressure of the subject using a blood pressure calculation algorithm based on the pulse transit time and the photoplethysmogram intensity ratio, according to equations (1) and (2):

$$DBP = \frac{a}{PIR} + b\frac{m}{h^2} + c; \text{ and} \tag{1}$$

$$SBP = \frac{a}{PIR} + b\frac{m}{h^2} + \frac{d}{PTT^2} + e; \tag{2}$$

wherein DBP is a diastolic blood pressure of the subject, SBP is a systolic blood pressure of the subject, PTT is the pulse transit time, PIR is the photoplethysmogram intensity ratio, m is a body weight of the subject, h is a height of the subject, and a, b, c, d, and e are constant coefficients.

2. The apparatus of claim 1, wherein each of the plurality of intrinsic mode functions has a characteristic frequency, values of characteristic frequencies of the plurality of intrinsic mode functions are different from each other.

3. The apparatus of claim 2, wherein the memory stores computer-executable instructions for controlling the one or more processors to select one or more of the plurality of intrinsic mode functions having characteristic frequencies outside a range of acceptable characteristic frequencies as the one or more first intrinsic mode functions.

4. The apparatus of claim 3, wherein the one or more first intrinsic mode functions are associated with low frequency baseline drifting.

5. The apparatus of claim 1, wherein the memory stores computer-executable instructions for controlling the one or more processors to:
   prior to decompose a first physiological signal, filter a high frequency noise from a second physiological signal to obtain the first physiological signal.

6. The apparatus of claim 1, wherein the one or more sensors are configured to detect an electrocardiography R-wave of the subject to acquire a second electrocardiography R-wave signal;

the memory stores computer-executable instructions for controlling the one or more processors to filter a high frequency noise from a second electrocardiography R-wave signal thereby obtaining the first electrocardiography R-wave signal.

7. The apparatus of claim 1, wherein the first physiological signal is decomposed into a function according to equation (3):

$$s(t) = \sum_{k=1}^{N} IMF_k(t) + r_N(t); \quad (3)$$

wherein s(t) is the first physiological signal; IMF stands for intrinsic mode functions; k is an integer, $1 \leq k \leq N$; N is an integer greater than 2; and $r_N(t)$ stands for a residual, which is a monotonic signal;

wherein the empirical mode decomposition algorithm comprises:

(a) identifying a maxima and a minima of the first physiological signal;
(b) calculating an upper envelop and a lower envelop based on the maxima and the minima;
(c) subtracting a mean of the upper envelop and the lower envelop from the first physiological signal to obtain a first mode of the plurality of intrinsic mode functions;
(d) subtracting the first mode from the first physiological signal to obtain a first residual;
(e) identifying a maxima and a minima of the first residual;
(f) calculating an upper envelop and a lower envelop of the first residual based on the maxima and the minima of the first residual;
(g) subtracting a mean of the upper envelop and the lower envelop from the first residual to obtain a second mode of the plurality of intrinsic mode functions; and
reiterating steps of (a) to (g) until the plurality of intrinsic mode functions and the residual are obtained, wherein the residual does not include a wave signal and cannot be decomposed any more.

8. The apparatus of claim 1, wherein calculate the denoised physiological signal comprises calculate a denoised photoplethysmogram signal according to equation (4):

$$ds(t) = \Sigma_{k=m}^{n} IMF_k(t) \quad (4);$$

wherein PPG stands for the denoised photoplethysmogram signal; IMF stands for intrinsic mode functions; k is an integer, $1 \leq k \leq N-1$; and N is an integer greater than 2.

9. The apparatus of claim 1, wherein calculate the denoised physiological signal comprises calculate a denoised photoplethysmogram signal according to equation (5):

$$ds(t) = \Sigma_{k=1}^{n} IMF_k(t) \quad (5);$$

wherein PPG stands for the denoised photoplethysmogram signal; IMF stands for intrinsic mode functions; k is an integer, $1 \leq k \leq n$; n is an integer less than N, and greater than or equal to 1; and N is an integer greater than 2.

10. The apparatus of claim 1, wherein calculate the denoised physiological signal comprises calculate a denoised photoplethysmogram signal according to equation (6):

$$ds(t) = \Sigma_{k=1}^{N-1} IMF_k(t) \quad (6);$$

wherein PPG stands for the denoised photoplethysmogram signal; IMF stands for intrinsic mode functions; k is an integer, $1 \leq k \leq N-1$; and N is an integer greater than 2.

11. A method of determining a blood pressure of a subject, comprising:

decomposing a first physiological signal corresponding to a first physiological parameter using an empirical mode decomposition algorithm into a sum of a plurality of intrinsic mode functions and a residual, wherein the first physiological parameter is a pulse wave; and the first physiological signal is a photoplethysmogram signal;

identifying one or more first intrinsic mode functions of the plurality of intrinsic mode functions that are associated with a noise signal, thereby obtaining one or more second intrinsic mode functions of the plurality of intrinsic mode functions that are different from the one or more first intrinsic mode functions;

calculating a denoised physiological signal by accumulating the one or more second intrinsic mode functions;

calculating a ratio of a photoplethysmogram peak intensity to a photoplethysmogram valley intensity in one cardiac cycle;

determining a photoplethysmogram intensity ratio based on the ratio of the photoplethysmogram peak intensity to the photoplethysmogram valley intensity in the one cardiac cycle;

obtaining a first electrocardiography R-wave signal of the subject;

determining a time interval between an electrocardiography R-wave peak of the first electrocardiography R-wave signal and a peak of a first derivative of the denoised physiological signal in one cardiac cycle;

determining a pulse transit time based on the time interval; and determining the blood pressure of the subject using a blood pressure calculation algorithm based on the pulse transit time and the photoplethysmogram intensity ratio according to equations (1) and (2):

$$DBP = \frac{a}{PIR} + b\frac{m}{h^2} + c; \text{ and} \quad (1)$$

$$SBP = \frac{a}{PIR} + b\frac{m}{h^2} + \frac{d}{PTT^2} + e; \quad (2)$$

wherein DBP is a diastolic blood pressure of the subject, SBP is a systolic blood pressure of the subject, PTT is the pulse transit time, PIR is the photoplethysmogram intensity ratio, m is a body weight of the subject, h is a height of the subject, and a, b, c, d, and e are constant coefficients.

12. The method of claim 11, wherein each of the plurality of intrinsic mode functions has a characteristic frequency, values of characteristic frequencies of the plurality of intrinsic mode functions are different from each other.

13. The method of claim 12, wherein identifying the one or more first intrinsic mode functions comprises selecting one or more of the plurality of intrinsic mode functions having characteristic frequencies outside a range of acceptable characteristic frequencies as the one or more first intrinsic mode functions.

14. The method of claim 13, wherein the one or more first intrinsic mode functions are associated with low frequency baseline drifting.

15. The method of claim 11, prior to decomposing the first physiological signal, further comprising:
filtering a high frequency noise from a second physiological signal thereby obtaining the first physiological signal.

16. The method of claim 11, further comprising:
measuring an electrocardiography R-wave of the subject to obtain a second electrocardiography R-wave signal; and
filtering a high frequency noise from a second electrocardiography R-wave signal thereby obtaining the first electrocardiography R-wave signal.

17. The method of claim 11, wherein the first physiological signal is decomposed into a function according to equation (3):

$$s(t) = \sum_{k=1}^{N} IMF_k(t) + r_N(t); \qquad (3)$$

wherein s(t) is the first physiological signal; IMF stands for intrinsic mode functions; k is an integer, $1 \leq k \leq N$; N is an integer greater than 2; and $r_N(t)$ stands for a residual, which is a monotonic signal;
wherein the empirical mode decomposition algorithm comprises:
(a) identifying a maxima and a minima of the first physiological signal;
(b) calculating an upper envelop and a lower envelop based on the maxima and the minima;
(c) subtracting a mean of the upper envelop and the lower envelop from the first physiological signal to obtain a first mode of the plurality of intrinsic mode functions;
(d) subtracting the first mode from the first physiological signal to obtain a first residual;
(e) identifying a maxima and a minima of the first residual;
(f) calculating an upper envelop and a lower envelop of the first residual based on the maxima and the minima of the first residual;
(g) subtracting a mean of the upper envelop and the lower envelop from the first residual to obtain a second mode of the plurality of intrinsic mode functions; and
reiterating steps of (a) to (g) until the plurality of intrinsic mode functions and the residual are obtained, wherein the residual does not include a wave signal and cannot be decomposed any more.

18. The method of claim 11, wherein calculating the denoised physiological signal comprises calculating a denoised photoplethysmogram signal according to equation (4):

$$ds(t) = \Sigma_{k=m}^{n} IMF_k(t) \qquad (4);$$

wherein PPG stands for the denoised photoplethysmogram signal; IMF stands for intrinsic mode functions; k is an integer, $1 \leq k \leq N-1$; and N is an integer greater than 2.

19. The method of claim 11, wherein calculating the denoised physiological signal comprises calculating a denoised photoplethysmogram signal according to equation (5):

$$ds(t) = \Sigma_{k=1}^{n} IMF_k(t) \qquad (5);$$

wherein PPG stands for the denoised photoplethysmogram signal; IMF stands for intrinsic mode functions; k is an integer, $1 \leq k \leq n$; n is an integer less than N, and greater than or equal to 1; and N is an integer greater than 2.

20. The method of claim 11, wherein calculating the denoised physiological signal comprises calculating a denoised photoplethysmogram signal according to equation (6):

$$ds(t) = \Sigma_{k=1}^{N-1} IMF_k(t) \qquad (6);$$

wherein PPG stands for the denoised photoplethysmogram signal; IMF stands for intrinsic mode functions; k is an integer, $1 \leq k \leq N-1$; and N is an integer greater than 2.

* * * * *